United States Patent
Drevet

(10) Patent No.: US 6,361,284 B2
(45) Date of Patent: Mar. 26, 2002

(54) VIBRATING MEMBRANE FLUID CIRCULATOR

(76) Inventor: Jean-Baptiste Drevet, 43 boulevard Saint-Michel, 75005 Paris (FR)

( * ) Notice: Subject to any disclaimer, the term of this patent is extended or adjusted under 35 U.S.C. 154(b) by 0 days.

(21) Appl. No.: 09/745,405

(22) Filed: Dec. 26, 2000

Related U.S. Application Data

(63) Continuation of application No. 09/117,982, filed as application No. PCT/FR97/00262 on Feb. 11, 1997.

(30) Foreign Application Priority Data

Feb. 12, 1996 (FR) ............................................. 96 01701

(51) Int. Cl.[7] ................................................. F04F 7/00
(52) U.S. Cl. ...................................... 417/240; 417/395
(58) Field of Search ......................... 417/410.1, 410.2, 417/241, 240, 555.1, 394, 395

(56) References Cited

U.S. PATENT DOCUMENTS

| | | | |
|---|---|---|---|
| 3,107,630 A | * 10/1963 | Johnson et al. | |
| 3,743,446 A | 7/1973 | Mandroian | 417/153 |
| 3,765,175 A | 10/1973 | Ohnaka | 417/240 |
| 4,063,826 A | 12/1977 | Riepe | 417/410 |
| 4,488,854 A | 12/1984 | Miller | 417/322 |
| 4,498,851 A | 2/1985 | Kolm et al. | 417/241 |
| 4,939,405 A | 7/1990 | Okuyama et al. | 310/330 |
| 5,525,041 A | * 6/1996 | Deak | 417/63 |

FOREIGN PATENT DOCUMENTS

| | | |
|---|---|---|
| DE | 3621766 A | 1/1988 |
| EP | 0 412 856 A | 12/1991 |
| SU | 244126 | 10/1969 |

OTHER PUBLICATIONS

Patent Abstracts of Japan, vol. 015, No. 164 (M–1106) Apr. 24, 1991; and JP 03 31590 A.
Patent Abstracts of Japan, vol. 009, No. 132 (M–385) 706.85 and JP 60 013994 a (Kaetsu Hoshi) Jan. 24, 1985.
Patent Abstracts of Japan, vol. 014, No. 496 (E–0996) Oct. 29, 1990 and JP 02 206339 A (Aisin Seiki Co., Ltd.) Aug. 16, 1990.
Patent Abstracts of Japan, vol. 015, No. 253 (M–1129) Jun. 27, 1991 and JP 03 081585 A (Mitsubishi Kasei Corp.) Apr. 5, 1991.

* cited by examiner

*Primary Examiner*—Willis R. Wolfe
*Assistant Examiner*—Mahmoud Gimie
(74) *Attorney, Agent, or Firm*—Nixon Peabody LLP; Stuart J. Friedman

(57) ABSTRACT

A vibrating membrane fluid circulator comprising an internal hydraulic circuit made up in succession of an admission orifice (1), a pump body (2), and a delivery orifice (3), the pump body (2) defining, in operation, a space (4, 18, 30) having rigid walls (5, 6) between which a deformable membrane (9) is placed having means for coupling its end (11) adjacent to the admission orifice to a motor member (39) generating a periodic excitation force substantially normally to the surface thereof, said membrane (9) being associated with means for creating tension parallel to the fluid circulation direction, said membrane constituting the medium for waves travelling from the end subjected to the excitation force towards its opposite end situated adjacent to the delivery orifice, said displacement being accompanied by forced damping due to the shape of the rigid walls so as to transfer energy from the membrane to the fluid giving rise to a pressure gradient and to fluid flow related to the dimensions of the pump body and of the membrane, the shape and the spacing of the rigid walls, the mechanical characteristics of the membrane, and the characteristics of its excitation and its tension state.

13 Claims, 5 Drawing Sheets

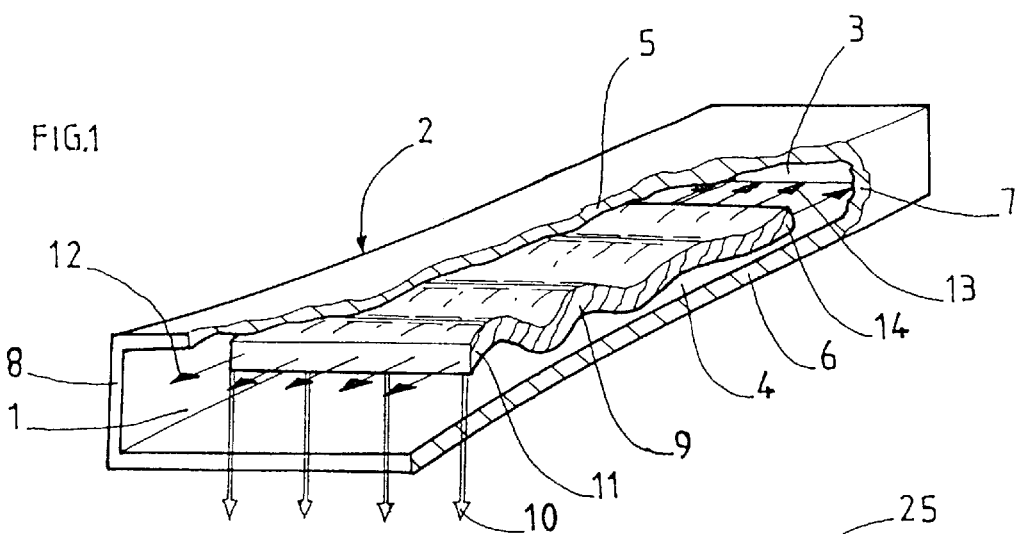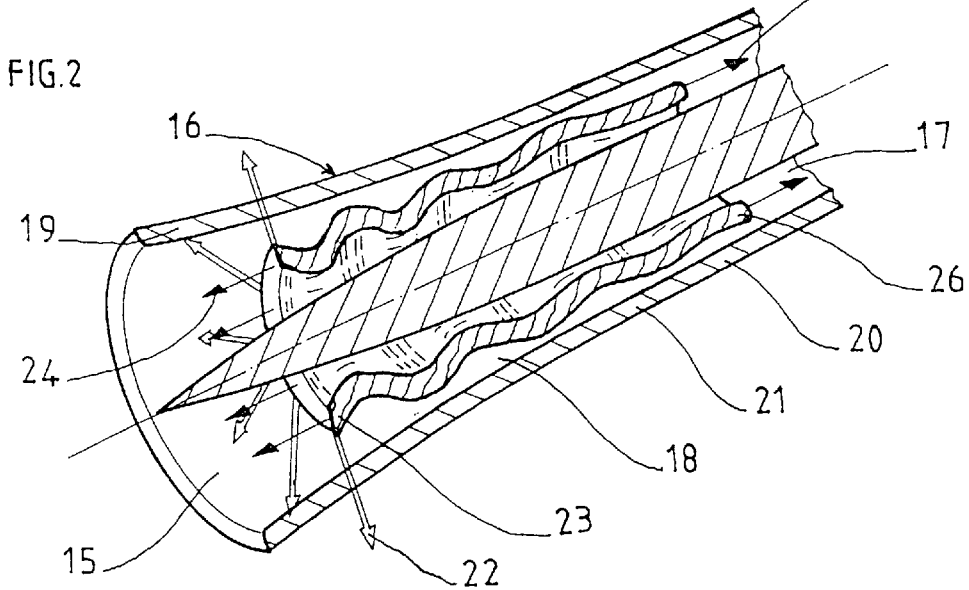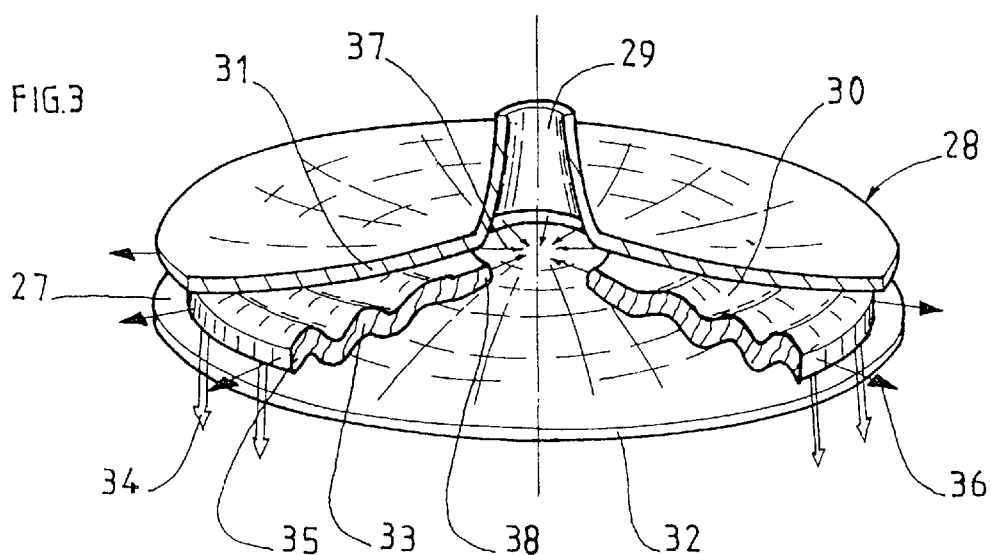

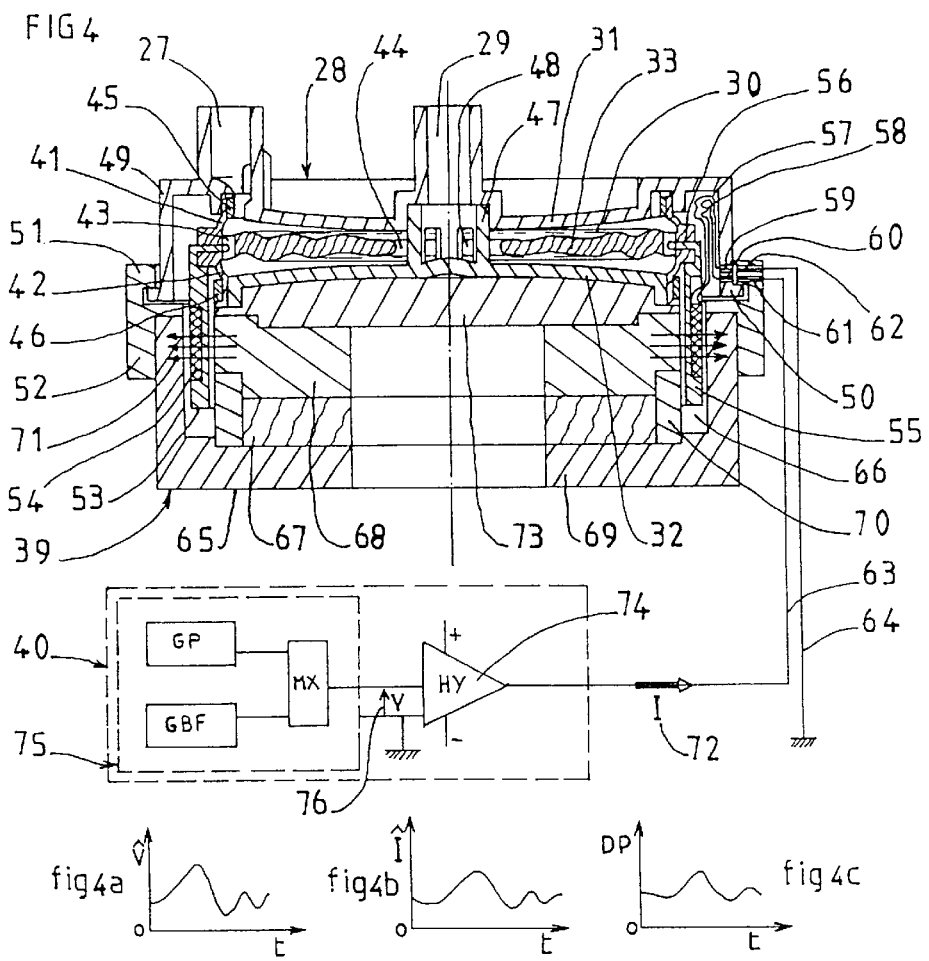

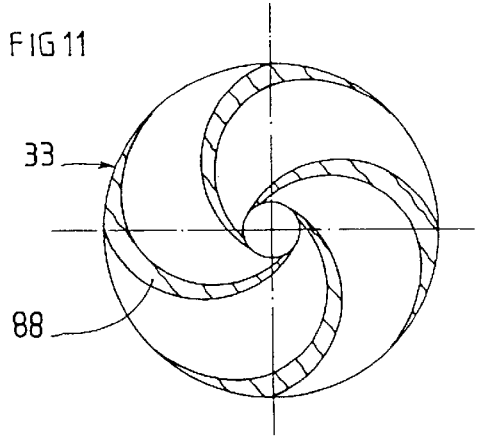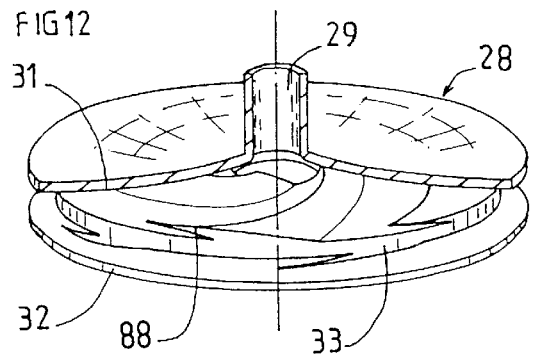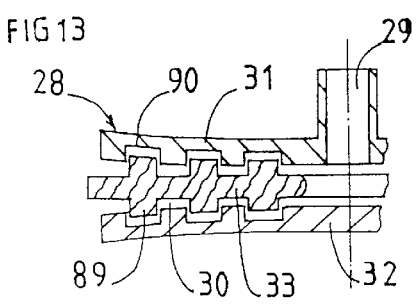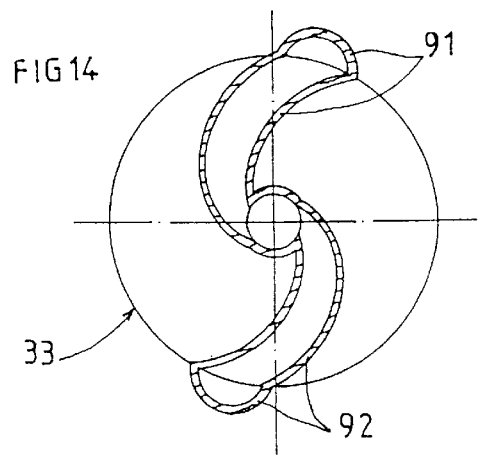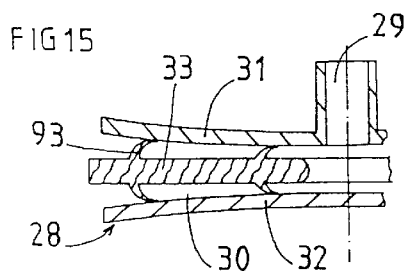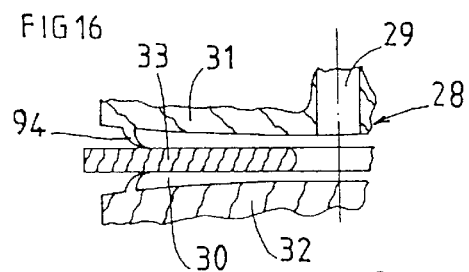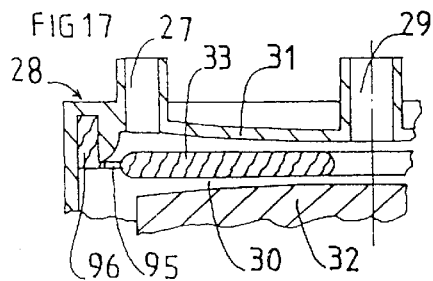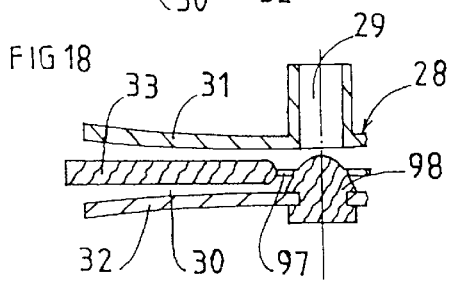

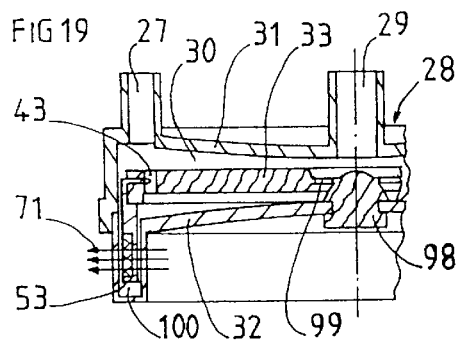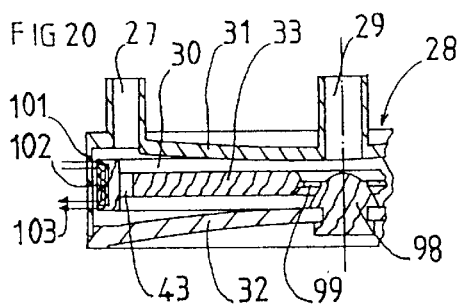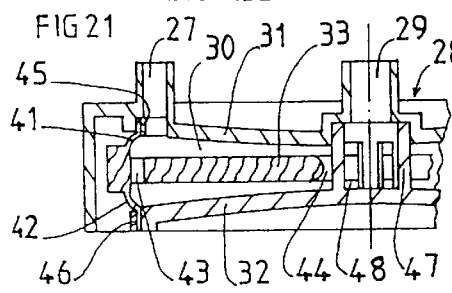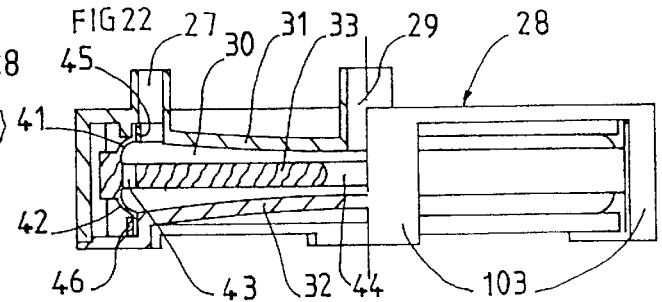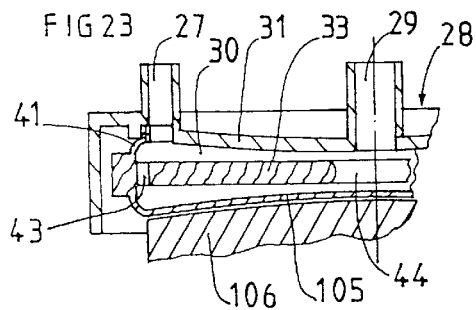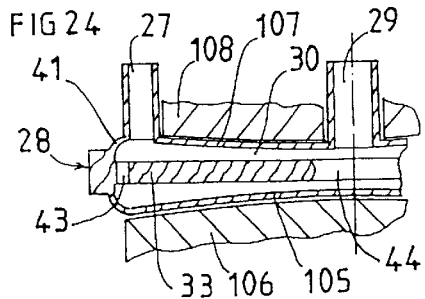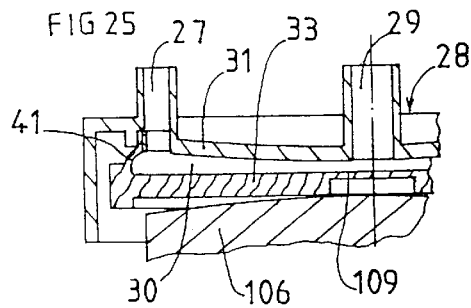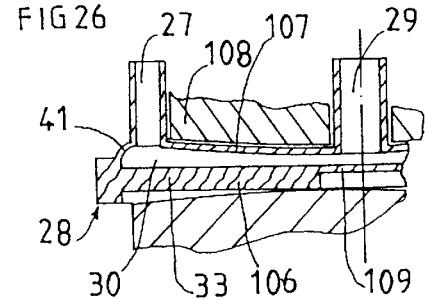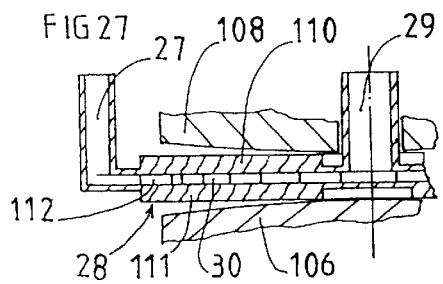

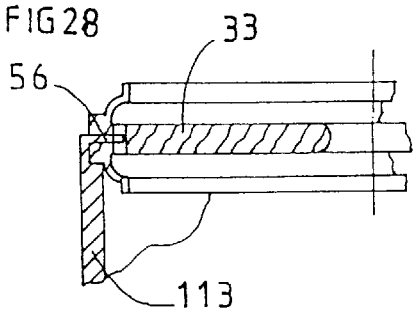
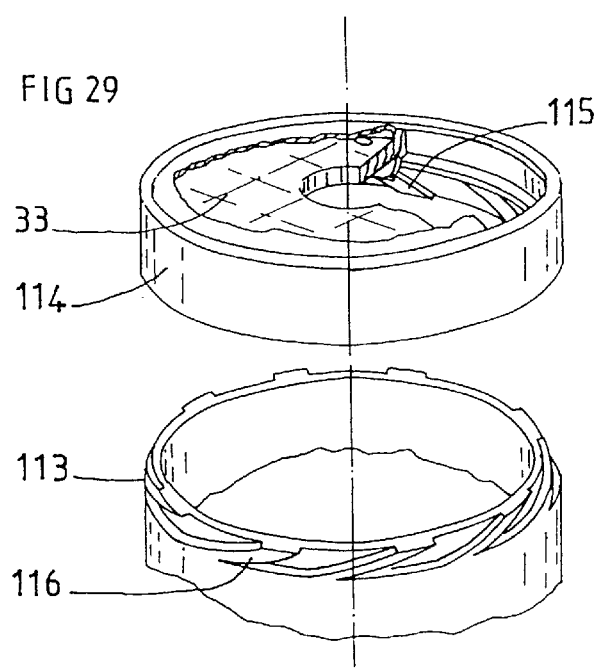
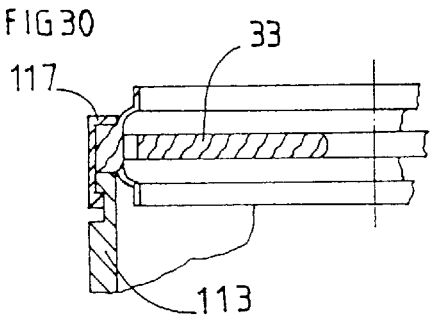
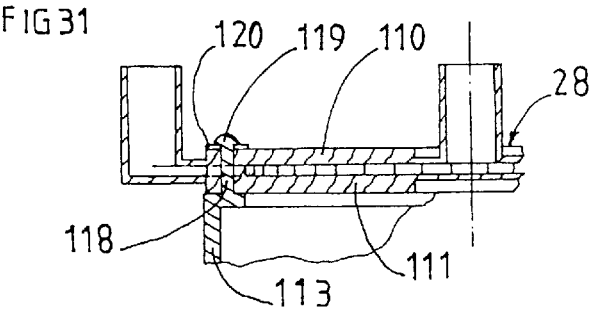
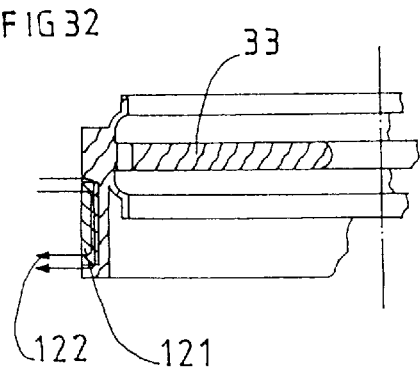
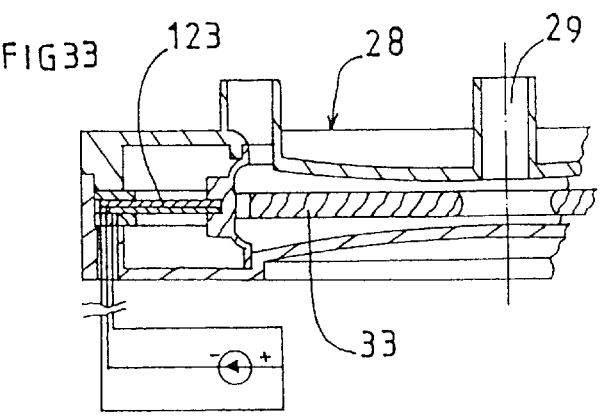

VIBRATING MEMBRANE FLUID CIRCULATOR

CROSS-REFERENCE TO RELATED APPLICATION

This application is a continuation of pending application Ser. No. 09/117,982, filed Aug. 11, 1998 which is a 371 of PCT/FR97/00262 filed Feb. 11, 1997.

The present invention relates to a vibrating membrane fluid circulator, in particular for biological fluids.

BACKGROUND OF THE INVENTION

Numerous types of pump are known both in industrial and in biomedical fields. The following can be mentioned:

reciprocating positive displacement pumps whose main elements are pistons or membranes associated with admission and delivery valves. Their main drawback lies in the cyclical aspect of their motion and in the presence of the valves;

so-called "peristaltic" positive displacement pumps in which continuously moving wheels deform and compress a flexible tubular pump body. The compression can be damaging for certain liquids to be pumped that include sensitive elements (e.g. blood);

"impeller" pumps such as centrifugal pumps based on a vaned rotor or a vortex. Their drawback lies in the high speed of rotation which generates shear in the fluid streams, friction, and cavitation, all of which phenomena can be damaging to fragile fluids; and axial turbine pumps in which fragile fluids suffer likewise from the same drawbacks as in the preceding pumps.

Also known is a vibrating-membrane fluid propulsion device, as described in document FR-A-2 650 862. That device provides a technical solution which is not always suitable for obtaining the hydraulic performance required by most industrial and biomedical applications.

SUMMARY OF THE INVENTION

The vibrating membrane fluid circulator of the invention proposes solutions whereby the fields of application of the circulator are enlarged, the hydraulic performance thereof is improved, the circulator is more compact, and finally the pump body can be for a single use only, which is advantageous in the biomedical field.

To this end, the fluid circulator of the invention comprises an internal hydraulic circuit successively made up of an admission orifice, a pump body, and a delivery orifice, the pump body defining, in operation, a space having rigid walls between which a deformable propulsion membrane is placed. The membrane has means for coupling its end situated adjacent to the admission orifice to a drive member for generating a periodic excitation force substantially normal to its surface. Provision is also made for means to keep the membrane under tension, thereby enabling it to constitute a medium for waves travelling from the end of the membrane subjected to the excitation force towards its opposite end. Displacement of these waves is accompanied by forced damping due to the shape of the rigid walls, so that mechanical energy is transferred from the membrane to the fluid, with this appearing in the form of a pressure gradient and of a fluid flow. The characteristics of the pressure gradient and of the fluid flow are related to the dimensions of the pump body, to the dimensions of the membrane, to the shape and the spacing of the rigid walls, to the mechanical characteristics and the tension state of the membrane, and to the parameters of the excitation applied thereto.

In a preferred embodiment, the periodic excitation of the membrane is implemented at one of its natural frequencies, and in particular at its first natural frequency. The values of such natural frequencies are associated with the mechanical characteristics of the membrane and with its tension state. The excitation frequency should be kept down to low values of the order of 40 Hz to 50 Hz so as to avoid localized pressure effects and shear effects between fluid streams.

In another embodiment, the space having rigid walls is defined by two disk-shaped walls, between which there is placed a deformable membrane that is also disk-shaped. This circular architecture possesses an effect whereby energy radiating from the outside towards the center of the system is concentrated, thereby making it possible to generate pressure gradients compatible with those required by industrial and biomedical applications. This solution also makes it possible to operate with very low excitation amplitudes at the periphery, thus making it possible to avoid injuring fragile fluids. Another advantage is that it makes it possible to tension the membrane very simply since it suffices to take action solely on the outside edge thereof.

In another embodiment, the membrane is made up of an assembly of superposed membranes, with the membranes being separated by fine spacers of a material having very low stiffness. This dispositions makes it possible to increase the mass of a membrane while retaining a natural frequency close to the natural frequency of each of the membranes when identical membranes are assembled together.

In another embodiment, flexible deflectors are carried by the membrane and press against the pump body. The deflectors modify the length of the hydraulic circuit and the way in which fluid flow speeds vary in the circulation space. This disposition enables the circulator to operate in association with rigid walls that are spaced further apart, which is favorable for propelling fluids that are fragile or that are laden with particles.

In another embodiment, circular flexible lips are carried by the membrane and bear against the pump body, the lips thus providing a simple non-return valve relative to the fluid flow, thereby satisfying requirements, particularly in certain biomedical applications.

In another embodiment, the circulator pump body forms a unit that integrates the following in inseparable manner: the membrane, the admission and delivery orifices, and the walls defining the space in which the membrane is housed. These walls are rigid and are held apart from each other by spacer means. At the periphery they are connected to the membrane via flexible walls. Inside the circulation space, the membrane has perforations at said periphery, and also a central orifice, thereby enabling the fluid to flow from one side of the membrane to the other. This technical disposition makes it possible to provide a pump body whose operation is not disturbed by the value of the admission pressure.

The membrane excitation means are constituted by an electromagnetic motor whose feed circuit for receiving excitation alternating current includes a power amplifier circuit and a circuit for generating an excitation signal so as to provide the possibilities of modulating amplitude, of programming, of storage, and of generating complex excitation signals, e.g. simulating heart beats.

BRIEF DESCRIPTION OF THE DRAWINGS

Other characteristics and advantages appear from the description given below of various embodiments of the invention.

Reference is made to the accompanying drawings, in which:

FIG. 1 is a longitudinal section view through a tubular pump body for a longitudinal type fluid circulator, said view being fragmentary and diagrammatic;

FIG. 2 is a longitudinal section view through a pump body of a cylindrical type fluid circulator;

FIG. 3 is a fragmentary and diagrammatic view in diametral section through the pump body of a circular type fluid circulator;

FIG. 4 is an overall view in diametral section through a first embodiment of the FIG. 3 device;

FIGS. 4a, 4b, and 4c are three curves as a function of time showing respectively the amplitude of the excitation signal, the amplitude of the motor excitation current, and the hydraulic pressure gradient of a pump in operation;

FIGS. 5 to 10 are radial half-sections through various membranes suitable for being implemented in the circulator of the invention;

FIGS. 11 and 12 are respectively a plan view and a perspective view of a membrane-including deflectors;

FIG. 13 is a radial half-section through a membrane having concentric portions in relief and received in its circulation space;

FIG. 14 is a diagram of a variant embodiment of the membrane in which the hydraulic circuit is limited relative to the surface area of the membrane;

FIG. 15 shows a membrane including non-return lips housed in its circulation space;

FIG. 16 is a radial half-section showing a circulation space fitted with a membrane in which the walls of the space include non-return lips;

FIGS. 17 and 18 show a variant embodiment of the circulator in which the membrane has flexible link elements linking it to the pump body;

FIGS. 19 to 27 are section views of various embodiments of pump bodies with incorporated membranes, thus making them removable or for single use;

FIGS. 28 to 30 show the link between the membrane and an excitation member in the pump bodies shown in FIGS. 21 and 22;

FIG. 31 shows another way of linking the membrane and the excitation member in a pump body of the type shown in FIG. 24;

FIG. 32 is a radial half-section showing a membrane including an element that is responsive to a magnetic field generated by the excitation member; and FIG. 33 is a radial half-section showing a pump body including an excitation motor element.

DETAILED DESCRIPTION OF THE PREFERRED EMBODIMENTS

The device of the invention shown in FIG. 1 comprises a hydraulic circuit made up in succession of an admission orifice 1, a pump body 2, and a delivery orifice 3. The pump body 2 is a flat tube of varying section which defines the circulation space 4 by rigid walls 5, 6, 7, and 8. In the space 4 there is housed a deformable propulsion membrane 9 which is in the form of a flexible elastomer strip of width equal to the distance between the walls 7 and 8. A motor member (not shown) generates a periodic excitation force 10 which is applied to coupling means at the end 11 of said membrane 9 adjacent to the admission orifice 1, said force being regularly distributed over the edge of the membrane and having a direction that is normal thereto. The membrane 9 is maintained under tension by members (not shown) developing forces 12 and 13 in opposite directions and applied to the ends 11 and 14 of the membrane. When excited, the membrane is thus a medium for waves travelling from the end 11 which is subjected to the excitation towards the other end 14 which is situated beside the delivery orifice. Wave displacement is accompanied by forced damping due to the shape and to the spacing of the rigid walls 5 and 6, with said spacing preferably decreasing going away from the admission orifice towards the delivery orifice.

The damping causes energy to be transferred from the membrane 9 to the fluid, with this being in the form of a pressure gradient and a flow of fluid.

Overall the circulator constitutes an energy transducer, successively transferring energy from the excitation motor to the membrane and then from the membrane to the fluid. The energy delivered by the exciter depends on various parameters such as the excitation force, the excitation frequency (which is preferably the first natural frequency of the membrane), and the amplitude of excitation which is itself associated with the excitation frequency and the force. It is thus possible to modulate the energy delivered by the exciter by acting on the various parameters that have an effect on the energy delivered to the membrane.

The mechanical energy in the membrane 9 must essentially be understood as a flow of mechanical energy propagating by means of the membrane from the excitation point 11 where energy is transferred from the exciter to the membrane, towards the other end of the membrane. This energy comprises a kinetic energy fraction and a deformation energy fraction, and there are physical limits on such operation. The transfer of energy from the membrane to the fluid takes place progressively along the length of the membrane with the waves simultaneously propagating and being damped.

The hydraulic energy of the fluid is expressed as the hydraulic power delivered by the circulator, i.e. the product of the flow rate multiplied by the pressure gradient, with the relationship between flow rate and pressure depending mainly on the dimensions of the pump body and of the membrane, and on the spacing and the shape of the rigid walls 5 and 6, this also taking into account the internal headlosses of the system.

A variant of the device is shown in FIG. 2, where the hydraulic circuit is cylindrical and comprises an admission orifice 15, a pump body 16, and a delivery orifice 17, the pump body defining the circulation space 18 between walls 19 and 20 that are rigid, circularly symmetrical, and coaxial. A deformable tubular membrane 21 is housed in the tubular space 18 and is made of silicone elastomer, for example. An excitation motor member (not shown) generates a radial and symmetrical distribution of periodic excitation forces 22, said distribution of forces being applied by means of a coupling to the end 23 of the tubular membrane 21 adjacent to the admission orifice. The membrane is held under axial tension between the admission and the delivery ends by means (not shown) generating an axial distribution of tension forces 24 and 25 in opposite directions applied to the ends 23 and 26 of the membrane.

FIG. 3 shows a circular variant of the device of the invention in which the hydraulic circuit comprises an admission orifice 27, a pump body 28, and a delivery orifice 29, the pump body 28 defining a circulation space 30 by means of rigid walls 31 and 32. In the disk-shaped space 30 of decreasing thickness, a deformable membrane 33 that is likewise disk-shaped is received. It is made of silicone elastomer, for example.

An excitation motor member generates a cylindrical and symmetrical distribution of periodic excitation forces 34, said distribution of forces being applied by means of a coupling at the peripheral end 35 of the membrane 33 adjacent to the admission orifice. The membrane is also held under tension by means (not shown) generating a distribution of radial forces 36 and 37 in opposite directions applied to the peripheral end 35 and to the central end 38 of the membrane 33. It will be observed that the tension forces are a direct result of the shape of the membrane to which diverging forces are applied via its outside edge 35.

The membrane thus becomes a medium for concentric waves which travel from its edge 35 towards its center, this displacement being accompanied by the waves being damped and by the fluid being propelled, as explained above. An effect which is peculiar to this variant lies in the way the energy propagating from the periphery towards the center is concentrated, thus making it possible to generate pressure gradients greater than those in the previously-described variants of the circulator.

FIG. 4 is an overall view of the circular circulator shown in FIG. 3. This circulator comprises three main subassemblies: a removable pump body 28 for single use; an excitation motor 39 fixed to the support structure thereof; and an electrical power supply 40.

The pump body 28 defines the disk-shaped fluid-propulsion space 30 in which the vibrating deformable membrane 33 is situated. This space 30 is defined firstly by top and bottom rigid walls 31 and 32, and secondly by flexible walls 41 and 42 connecting the membrane 33 to the walls 31 and 32 at the periphery. The membrane 33 and the flexible walls 41 and 42 form a single piece of molded silicone elastomer, polyurethane, rubber, or the like.

Inside the space 30, the membrane 33 has peripheral perforations 43 and a central orifice 44 enabling the fluid to flow from one side of the membrane to the other. The edges of the flexible walls 41 and 42 are fixed to the rigid walls 31 and 32 by adhesive and by being clamped by means of rings 45 and 46, e.g. stainless steel rings. The walls 31 and 32 are connected to each other, centered, and held at the proper spacing by a spacer 47 carried by the top wall 31, assembly being performed by adhesive or by ultrasonic welding. The spacer 47 has orifices 48 to pass the fluid into the delivery orifice. The top wall 31 carries the delivery orifice 29 in its center and the admission orifice 27 at its periphery. It also has an outer skirt 49 protecting the sides of the pump body 28. This skirt is terminated by flange portions 50 which co-operate with collar portions 51 of a link ring 52 secured to the motor 39. The pump body is fixed to the motor by a bayonet fixing. The rigid walls 31 and 32 are molded out of a biocompatible rigid plastics material of the polysulfone kind.

In this variant of the pump body, the membrane 33 has a moving coil 53 at its periphery constituting the moving element of the excitation motor 39. This moving coil 53 has a winding of insulated conductor wires 54 mounted on a rigid coil support 55 that is thin and cylindrical. At its top edge the coil support 55 has a rigid collar 56 which is perforated and which penetrates into the membrane 33 to be fixed thereto by adhesive or by overmolding. Feed wires 57 and 58 connect the winding 54 to connectors 59 and 60 carried by the skirt 49, said connectors 59 and 60 making contact with connectors 61 and 62 carried by the link ring 52 and themselves connected to the electrical power supply of the circulator by wires 63 and 64. The coil support 55 is made of a plastics material having high mechanical strength and great dimensional stability, such as glass fiber reinforced polycarbonate.

The motor 39 has a moving coil 53 as described above and a magnetic circuit 65 which is stationary and which includes a gap 66 in which the winding 54 of the coil 53 moves. The magnetic circuit 65 comprises a permanent magnet 67, an internal polepiece 68, and an external polepiece 69 on opposite sides of the permanent magnet 67 and centered relative to each other by a spacer 70. The space between the two polepieces forms the gap 66 in which the winding 54 can move and in which there obtains a fixed permanent magnetic field 71 extending in a radial direction. The excitation forces 34 (see FIG. 3) are distributed as a result of electromagnetic induction applied to the portion of the winding 54 carrying an alternating excitation current 72 and immersed in the magnetic field 71 of the gap.

A cover 73 enables the pump body 28 to be centered and properly positioned on the excitation motor 39. The polepieces 68 and 69 have high magnetic permeability, being made of soft ferrite or of mild steel, for example. The permanent magnet 67 is made of a magnetic material of the rare earth, hard ferrite, etc. . . . type. It will be observed that the magnet and the polepieces can be obtained by molding a composite material comprising a matrix of plastics material within which there is dispersed a powder of magnetic material. The spacer 70, the cover 73, and the ring 52 are made of non-magnetic material.

The power supply circuit 40 delivering the excitation current 72 to the winding 54 comprises a power amplifier 74 and a signal generator 75. The power amplifier 74 is a standard audio type hybrid circuit of characteristics that are well adapted to this application. The generator 75 feeding the amplifier 74 essentially comprises three elements: an oscillator; a modulator; and a mixer. The oscillator generates a basic alternating signal of fixed amplitude and frequency which is the natural frequency of the membrane 33. The modulator has the ability to be programmed and to store data, and it generates the periodic signal for modulating the amplitude of the basic signal. The mixer circuit modulates the basic signal with the modulation signal to deliver an excitation signal 76. The way in which the circulator is powered electrically makes it possible for it to operate in the manner illustrated by the time curves shown in FIGS. 4a, 4b, and 4c. FIG. 4a is a graph showing the amplitude of the excitation signal 76, FIG. 4b shows the amplitude of the excitation current 72, and FIG. 4c shows the pressure gradient generated by the circulator. It is thus possible to generate pressure pulse cycles reproducing heart beat cycles for a biomedical application to extracorporeal circulation of the blood.

The membrane 33 shown in FIG. 5 is a composite membrane formed by assembling three similar membranes 77, 78, and 79 which are superposed and separated by two fine spacers 80 and 81 of very low stiffness. Assembly is performed by means of adhesive, the membranes being made of elastomer, and the spacers being made of elastomer foam. This disposition makes it possible to provide a membrane whose natural frequency is close to the natural frequency of each of the membranes, but with mass that is three times greater than the individual mass of any one membrane.

In FIG. 6, the membrane 33 has a core 82 of determined stiffness covered by a thickness 83 of a different material having lower stiffness than the core 82. For example, the core is made of a hard elastomer (80 on the Shore A scale) while the layer 83 is made by overmolding an elastomer gel having a Shore A hardness of about 20 (silicone or polyurethane).

In this disposition, the stiffness of the membrane is close to that of the core, while its mass is considerably greater than that of the core, thereby making it possible to obtain a natural frequency that is lower than that of the core on its own.

In the membrane 33 of FIG. 7, inclusions 84 are placed in a silicone or polyurethane elastomer. An inclusion may be of high or low density. This disposition makes it possible to modulate the mass distribution in the membrane 33 and thus to modify its vibration modes and the amplitude profile of the vibration. This embodiment gives great freedom in designing the outer profile of the membrane so that it can be matched to the flow parameter of the fluid.

The diagram of FIG. 8 shows a propulsion membrane 33 which is homogeneous, but of thickness e which varies as a function of radius r and of angular location, with this being for the purpose of modulating the stiffness and of distributing masses so as to improve and optimize the dynamic characteristics of the membrane.

FIG. 9 shows a membrane 33 made of elastomer, and having circular rigid pieces 85 and 86 at its peripheral and center ends 35 and 38, which pieces are assembled together by adhesive or overmolding. These pieces increase the stiffness of the membrane and above all they constitute elements which create radial internal tension in the membrane associated with deformation stresses. It is thus possible to modify the natural frequencies of the membrane without increasing its mass. The pieces 85 and 86 are made of a biocompatible rigid plastics material of the polysulfone kind. It will be observed that the role of the piece 85 is performed by the rigid support 55 in FIG. 4.

FIG. 10 shows another variant of the membrane 33 in which a structure 87 of rigid plastics material is integrated by partial overmolding. This structure 87 makes it possible to modify the stiffness of the elastomer membrane and is suitable for co-operating with the coupling for coupling said membrane to the excitation motor member 39.

The above-described examples for adjusting the stiffness of the membrane are not limiting: it is possible to act on the composition of the materials constituting the membrane or to integrate in a given material other types of stiffening structure, or indeed to shape the membrane so that it has ribs, for example.

FIGS. 11 and 12 show a particular variant of the membrane 33 having flexible deflectors 88 bearing against the rigid walls 31 and 32 of the pump body. The membrane 33 and its deflectors 88 constitute a single piece formed by molding elastomer. The deflectors 88 increase the length of the hydraulic circuit and modify the way in which fluid flow speeds vary in the circulation space 30. It is thus possible to make a circulator in which the spacing between the walls 31 and 32 is large, as is desirable for applications in which a particle-laden fluid is to be propelled, as is the case for pumps in washing machines and dishwashers.

FIG. 13 shows another technical disposition for acting on the flow parameters in the circulation space 30. Concentric projections 89 carried by the membrane 33 and concentric grooves 90 formed in the walls 31 and 32 co-operate to lengthen the hydraulic circuit and to reduce the section of said circuit in the space 30. This embodiment is particularly applicable to pumps of the type having low flow rate and high pressure gradient, such as micropumps for appliances such as steam irons or vehicle windshield washers.

In FIG. 14, the circulation space 30 is defined by flexible walls 91 and 92 defining and reducing the area of said space compared with the area of the membrane 33. This increases the pressure gradient created by the circulator, and such pumps are applicable to conditions of use that require low flow rates and high pressure gradients. The membrane 33 and the flexible walls 91 and 92 form a single piece molded out of elastomer.

In FIGS. 15 and 16, the hydraulic circuit includes non-return valves for the fluid. These valves are simply made by means of circular flexible lips disposed in the circulation space 30 between the fixed walls and the membrane. In FIG. 15, the lips 93 are carried by the membrane 33 and are integrally formed therewith, being molded out of elastomer material, while in FIG. 16 the flexible lips are carried by the walls 31 and 32. This type of embodiment is applicable to certain types of biomedical pump.

The deflectors 88, projections 89, walls 91, 92 or lips 93, 94 of FIGS. 12 to 16 can be implemented as elements separate from the membrane and the pump body and can be held in place by jamming means and appropriate mutual shapes in the circulation space.

In FIGS. 17 and 18, the membrane 33 is connected to the pump body 28 in flexible manner by a web which extends it and which terminates in a fixing piece embedded in and stuck to the pump body 28. The web includes perforations allowing fluid to circulate and is integrally formed with the membrane and the fixing piece, e.g. being molded out of elastomer. This link ensures that the membrane is centered in the pump body and limits the amplitude of movement at the end of the membrane extended by the web, particularly when priming the circulator. In FIG. 17, the web 95 extends the membrane beyond its outer edge and terminates in a circular piece whose periphery is embedded in the wall 31, while in FIG. 18, the web 97 extends the inner end of the membrane and terminates in a central stud 98 embedded in the wall 32.

FIGS. 19 and 20 show two variant embodiments of a single-use pump body of a circular type circulator. These variants are of the type having a box that is rigid and closed.

Thus, the rigid walls 31 and 32 are the top and bottom walls of a closed box; between them they define a circulation space 30, said box having an admission orifice 27 and a delivery orifice 29 through its wall 31 and containing the propulsion membrane 33 inside the circulation space 30. The membrane is centered relative to the housing in these figures, as in FIG. 18, by means of a stud 98 connected to the inner end of the membrane by a web 97 which includes perforations 99. As in FIG. 4, the membrane also has peripheral perforations 43, these perforations serving to allow the fluid to circulate. In the embodiment of FIG. 19, the box has an annular housing 100 of narrow width with fine and rigid walls housing a moving excitation coil 53 secured to the membrane 33 as in FIG. 4. In operation, the housing 100 is placed in the gap of the magnetic circuit of an excitation motor, with the magnetic field 71 of the gap passing through the housing 100. In FIG. 18, the box is made in a different form: at its periphery it has a fine and rigid wall 101 facing a polepiece 102 of magnetic material of the soft ferrite type which is secured to the membrane 33. In operation, this wall 101 is placed in the gap of a multipolar magnetic circuit passing via the polepiece 102, the magnetic field 103 of the motor entering and leaving via the same wall 101.

FIGS. 21 and 22 show two other variant embodiments of a pump body for single use, i.e. a discardable pump body. This embodiment differs from that of the two preceding figures in that it has flexible walls 41 and 42 connecting the periphery of the membrane 33 to the rigid walls 31 and 32, thereby defining the circulation space 30 independently of the rigid structure carrying the walls 31 and 32. As in FIG.

4, this makes it possible to provide direct coupling between the membrane and the moving member of an excitation motor via the membrane portion which projects outside the walls 41 and 42. The pump body shown in FIG. 21 has a central portion similar to that shown in FIG. 4. However, the embodiment shown in FIG. 22 has a link between the two rigid walls 31 and 32 via four spacers 103 which interconnect their peripheries. Spaces 104 between these spacers serve to receive means for couping the membrane to the excitation motor member.

The embodiment of the pump body shown in FIG. 23 differs from that of FIG. 22 by the fact that the circulation space is not directly defined by a rigid wall such as 32, but by a flexible wall 105 which extends the web 42 and closes the bottom portion of the circulation space. In this case, the structure of the motor includes a rigid wall 106 on which the flexible wall 105 comes to rest when the pump body is coupled to the excitation motor 39. This rigid wall 106 is not discardable.

In FIG. 24, there can be seen another variant similar to that of FIG. 23, i.e. the pump body which includes the membrane is defined by two flexible walls 105 and 107 which, when in operation, co-operate with two rigid walls 106 and 108 of the pump so as to define the circulation space. In this case, the top flexible wall 107 is integral firstly with the flexible wall 105 and the membrane 33, and secondly with the endpieces 27 and 29 constituting the admission orifice and the exhaust orifice for the fluid circulation space. In operation, the pump body is inserted between the rigid walls 106 and 108 which belong to the structure of the circulator and which are not discardable, and the membrane 33 is coupled to the excitation motor 39.

The variant embodiments of the pump body shown in FIGS. 25 and 26 differ from the embodiments of FIGS. 23 an 24, respectively, by the absence of the wall 105. In other words, fluid situated in the circulation space 30 co-operates with only one face of the membrane 33, i.e. its face opposite from its face situated facing the piece 106. In this case, the membrane has no orifices 43 and 44, and the central orifice 44 is closed by a web 109. The two pump bodies of FIGS. 25 and 26 are shown in the same manner as the two pump bodies of FIGS. 23 and 24, respectively.

FIG. 27 is on the same lines as the embodiments of FIGS. 25 and 26, showing an embodiment in which the circulation space is defined between two membranes 110 and 111 that are spaced apart from other by spacers 112 and that are put into operation between fixed pieces 106 and 108 of profile identical to that of the fixed walls 31 and 32 as described above. The circulation space 30 is connected to an admission orifice 27 in flexible manner and also to a delivery orifice 29, the endpieces constituting said orifices being integral with the two spaced-apart membranes, and the assembly constituting the pump body being discardable, i.e. for a single use only. It will be observed that in this embodiment, proper operation requires the admission pressure to be positive.

FIG. 28 shows in isolation the simple and low cost mechanical link between the membrane 33 and a moving element 113 of the excitation motor for the purpose of applying the excitation drive forces 34 to the membrane. The moving element 113 is extended, as in FIG. 4, by a rigid collar 56 that is perforated and that penetrates into the membrane 33 where it is held fixed by adhesive or overmolding. The moving element 113 can be the support of a coil or the support of a moving member made of magnetic material.

FIG. 29 shows another way of linking the membrane 33 to the element 113 belonging to the excitation member. The membrane 33 is embedded at its periphery in a ring 114 which is provided with threads 115 making it possible for the ring 114 to engage complementary threads 116 on the element 113 so as to be coupled thereto. Other forms of coupling, in particular of the bayonet type, can be suitable.

FIG. 30 shows another way of coupling the membrane 33 to the moving piece 113 by means of an outer collar 117 so that the membrane is peripherally clamped on the top edge of the moving element 113.

The linking shown in FIG. 31 concerns variants of the pump bodies shown in FIG. 27. The moving element 113 of the exciter has studs 118 on its top edge which pass through the pump body 28 formed by the two associated membranes 110 and 111, with each stud having at its end a projection 119 co-operating with a clip 120 that clamps the membrane and holds it captive.

The embodiment of FIG. 32 has a membrane 33 whose periphery has an overmolded element 121 integral therewith, e.g. a coil or a magnetic member, said element 121 being suitable for responding to a magnetic field 122 generated by the excitation motor. The advantage of this disposition is lower manufacturing cost since the support is omitted from the element that is responsive to magnetic fields.

In FIG. 33, the membrane 33 is coupled to an element 123 which constitutes a piezoelectric excitation motor, that is particularly suitable for micropumps.

To obtain variation in the tension of a deformable membrane as implemented in circulators of the invention, it is possible to incorporate in the ends of said membrane, regardless of whether it is plane, tubular, or circular, elements that are responsive to a magnetic field and which, when properly oriented, enable said tension to be varied and thus enable the natural frequency of the membrane to be varied. This provides the ability to modulate the hydraulic power of the circulator without increasing the stroke of the exciter or the amplitude of the waves.

For example, in the membrane shown in FIG. 32, the elements 121 include a coil or material responsive to magnetic fields generated by an electromagnetic traction member, i.e. in a radial direction, said member being carried either by the excitation motor, or by the pump body itself.

It should be mentioned that the various shapes shown in FIGS. 1, 2, and 3 for circulators of the invention are adapted to particular applications. Thus, concerning the shape of FIG. 1, the circulator is particularly applicable to propulsion devices that are required to deliver a high flow rate with a low pressure gradient. The geometry shown in FIG. 2 relates more particularly to pumps that are compact and that provide a low flow rate. As for FIG. 3, circulators of circular shape apply to the largest number of applications with greater pressure gradients being available.

The various dispositions described above can be used to make rigid cassettes which incorporate firstly the pump bodies and which can secondly associate numerous additional functions, in particular those concerning connection of the pump to upstream and downstream hydraulic circuits, and the functions of measuring pressure, measuring flow rate, filtering, degassing, processing the fluid, and functions of adding substances such as medicaments, tracers, analysis substances, . . . . Applications for such rigid cassettes can then be found in making dialysis cartridges, extracorporeal circulation cartridges including oxygenation of the blood, or cartridges for injecting insulin.

What is claimed is:

1. A membrane fluid circulator comprising an internal hydraulic circuit made up in succession of an admission orifice, a pump body and a delivery orifice wherein the pump body has rigid walls defining therebetween a circulation space for the fluid with a deformable membrane maintained in tension parallel to the fluid circulation direction and located in said circulation space, said rigid walls being disk-shaped with said delivery orifice arranged at the center of at least one of said walls and said deformable membrane being disk-shaped, said membrane having an edge near to said admission orifice and provided with means for coupling to a motor member generating a periodic excitation force substantially normally to the surface of said membrane, said membrane constituting a medium for waves traveling from said admission orifice to said delivery orifice, and wherein the thickness of said circulation space is decreasing from said admission orifice to said delivery orifice for acting as forced damping means of the waves along said membrane.

2. A fluid circulator according to claim 1, wherein said disk-shaped membrane has a central orifice.

3. A fluid circulator according to claim 1, wherein said membrane is integral with a peripheral flexible wall secured to the periphery of said one of said disk-shaped rigid walls provided with said delivery orifice.

4. A fluid circulator according to claim 3, wherein said membrane is integral with a second peripheral flexible wall secured to the periphery of said other rigid wall, said membrane being provided with peripheral perforations and with a central orifice and said one rigid wall is provided with said admission orifice.

5. A fluid circulator according to claim 4, wherein said rigid wall provided with said admission and delivery orifices comprises means for detachably securing said pump body to said motor member.

6. A fluid circulator according to claim 1, wherein one of said rigid walls is provided with said admission and delivery orifices, said membrane being integral with a peripheral flexible wall secured to the periphery of said one rigid wall, so that said one rigid wall and membrane form a disposable assembly detachably connectable to said second rigid wall.

7. A fluid circulator according to claim 6, wherein said membrane has peripheral perforations and a central orifice and is integral with a flexible wall which rests on said second rigid wall when the disposable assembly is connected thereto.

8. A fluid circulator according to claim 1, wherein said membrane is peripherally provided with a thin cylindrical coil located in the gap of a stationary magnetic field generator.

9. A fluid circulator according to claim 1, wherein the membrane is a composite body obtained by assembling together a plurality of portions having different mechanical characteristics.

10. A fluid circulator according to claim 1, wherein the hydraulic circuit includes reliefs between the membrane and the pump body, which reliefs act on the flow characteristics of the fluid.

11. A fluid circulator according to claim 1, wherein the pump body forms a unit integrating said membrane, said admission and delivery orifices, and said walls of the space in which the membrane is housed in inseparable manner, said pump body itself being separable from the motor member.

12. A fluid circulator according to claim 1, comprising an electromagnetic motor generating a periodic excitation force and fed with an alternating excitation current of intensity which is modulated to modulate the excitation force and thus the hydraulic power delivered by the circulator.

13. A fluid circulator according to claim 1, including at least one electromagnetic traction member generating radial forces applied to the periphery of the membrane to adjust the tension of the membrane in the direction of the waves travel.

* * * * *